United States Patent [19]

Adrion et al.

[11] 4,044,782
[45] Aug. 30, 1977

[54] ACID TREATED POLYESTER POLYURETHANE FOAM END WRAP

[75] Inventors: David Martin Adrion, Phoenix, Ariz.; Lloyd Bruce Hartsough, Cincinnati, Ohio

[73] Assignee: The Procter & Gamble Company, Cincinnati, Ohio

[21] Appl. No.: 670,594

[22] Filed: Mar. 26, 1976

[51] Int. Cl.² ............................................. A45D 7/00
[52] U.S. Cl. ................................... 132/7; 132/36.2 R
[58] Field of Search ........................... 132/7, 36.2, 40; 424/71, 72

[56] References Cited

U.S. PATENT DOCUMENTS

| | | | |
|---|---|---|---|
| 3,345,993 | 10/1967 | Haefele | 132/36.2 R |
| 3,847,165 | 11/1974 | Patel | 424/72 |
| 3,955,586 | 5/1976 | Hartsough | 424/71 |
| 3,975,515 | 8/1976 | Wajaruff | 424/71 |

*Primary Examiner*—G.E. McNeill
*Attorney, Agent, or Firm*—Douglas C. Mohl; George W. Allen; John A. O'Toole

[57] ABSTRACT

A superior end wrap comprising a particular type of open-celled polyurethane foam of specified porosity and thickness which foam has been treated with certain types of weak carboxylic acids. Also disclosed is a permanent waving process using said acid treated end wraps.

9 Claims, No Drawings

ACID TREATED POLYESTER POLYURETHANE FOAM END WRAP

BACKGROUND OF THE INVENTION

1. Field of the Invention

This invention relates to acid treated polyurethane foam end wraps for use in the cold permanent waving of hair. Further, the invention relates to the process of using the treated end wraps in cold permanent waving.

2. Prior Art

Cold permanent waving of hair has been a popular means of waving hair for a number of years. This popularity is due to the greater convenience for this method over other methods where externally applied heat is needed to achieve the desired result. This additional convenience has permitted nonprofessional consumers to wave their hair in their own homes. In cold waving, the waving is accomplished by applying a reducing agent to the hair which causes the hair to be "softened" (the disulfide linkages present in the keratin of hair are broken). This reducing step may be done after the hair has been sectioned into individual tresses but before it has been rolled onto curlers, after the rolling has been accomplished or at both times. After sufficient time has elapsed the hair is rinsed and neutralized by chemical or air oxidation, which step reforms the disulfide linkages broken in the aforementioned reducing step.

Cold permanent waving is not without its problems however. The materials are oftentimes somewhat difficult to use with the desired result not always achieved. For example, the ends of the hair present particular problems from a handling point of view, as well as from a hair damage point of view. In the varying process, the free ends of the hair must be wound about a cylindrical body (a curler) and this presents some difficulty. To overcome this problem most commercial waving kits contain small square or rectangular pieces of paper or other material (end wraps) which are folded and placed around a hair tress in such a manner that they embrace the free end of the tress.

Among the types of materials which have been used for the end wrap are permeable polyester and polyether polyurethanes as disclosed by Haefele in U.S. Pat. No. 3,345,993, issued Oct. 10, 1967; impermeable polyester and polyether polyurethane as disclosed by Haefele in U.S. Pat. No. 3,465,759, issued Sept. 9, 1969; and paper as disclosed by Bonilla in U.S. Pat. No. 2,991,790, issued July 11, 1961. Of these materials, permeable polyurethane foams prepared by condensation of organic isocyanates with polyesters are especially useful. Such polyester polyurethanes have excellent solvent resistance, color stability in the presence of ultraviolet light and are comparatively resistant to development of static charge.

All of these types of end wraps which have been disclosed in the prior art are well known to be helpful in the winding process. However, they do not fully protect the ends of the hair. The desirability of protecting the ends of the hair in permanent waving stems from the fact that repeated use of conventional waving procedures is often accompanied by an overexposure of the hair ends which are susceptible to damage because of the age of the hair at the ends and the stress the ends are expose to during the winding process. Such ends, when subjected to renewed cold waving treatments, generally exhibit undue frizziness, curling, harshness and drying because frequent treatment is believed to unduly stress and overexpose the hair ends in renewing or repeating the waving process.

There have been attempts in the past to treat certain types of end wraps with chemical agents so that the waving solution is counteracted before reaching the hair ends (See, for example, the aforementioned Bonilla reference and the concurrently filed application of Adrion and Hartsough having Ser. No. 670,940. Also included in some prior art attempts was the treatment of paper end wraps with citric acid to counteract the waving solution and thereby protect hair ends.

While it would be highly desirable to treat end wraps of the preferred polyester polyurethane material with waving solution counteractant, certain of such common counteractant chemicals are not compatible with this particular type of end wrap polyurethane. Some agents such as citric acid, for example, tend to degrade and discolor polyester polyurethane. There is thus a continuing need to identify and select compatible materials for use in realizing preferred treated end wraps for cold permanent waving products and methods.

Accordingly, it is an object of this invention to provide effective acid treated end wraps which are useful in the keratin modification process.

It is a further object of this invention to provide such treated end wraps which are made with preferred compatible end wrap and acid treatment materials.

It is a further object to provide an improved method for permanently waving hair by utilizing treated end wraps made from preferred materials.

It has been surprisingly discovered that by selecting particular types of weak carboxylic acids for use with polyester polyurethane end wraps, the above objectives can be realized and end wraps prepared which are superior to similar articles of the prior art.

SUMMARY OF THE INVENTION

The present invention is directed to end wraps for use in permanent waving processes. The end wraps comprise permeable flexible wafers of open-celled polyester polyurethane foam containing a solid sparingly-soluble, weak carboxylic acid to the extent of at least 5 milligrams of acid per cubic inch of foam.

The foam wafers have a thickness ranging from about one-sixteenth inch to about one sixty-fourth inch and an average pore incidence of from about 30 to about 120 pores per linear inch. The carboxylic acid has a $pK_1$ between about 2.5 and about 6.0 and a water-solubility of from about 0.1 to 10.0 parts acid per 100 parts water at 15° – 20° C.

The present invention is also directed to a process for imparting a permanent wave to hair. Such a process comprises the steps of forming the hair into tresses, wrapping about the end of each tress a flexible, acid-treated end wrap of the type decided above, winding each tress on a cylindrical body, saturating each wound tress with a keratin-reducing composition and thereafter neutralizng the action on the hair of said keratin reducing composition.

DETAILED DESCRIPTION OF THE INVENTION

The present invention resides in the discovery of an improved end wrap comprising a particular type of porous polyester polyurethane foam wafer treated with a particular type of carboxylic acid.

Polyester Polyurethane Foam End Wrap Material

The polyurethane foam material used for the end wrap wafer in the invention herein can be characterized as "polyester polyurethane." Polyurethanes are, of course, prepared by condensing polyols with organic isocyanates. Polyurethane foams are divided into two major categories depending on the type of polyol used in preparation — either "polyether" polyols or "polyester" polyols. The "polyester" foams are the materials utilized in this invention. These polyurethane foams can be prepared by a variety of methods which are well known in the art. Essentially, such foams are made by the condensation of organic isocyanates, such as tolylene diisocyanate, with polyesters such as the condensation product of adipic acid with polyethylene ether glycol, in the presence of a catalyst and a blowing agent. Basic processes and apparatus for preparing such polyester polyurethane foams are disclosed, for example, in Hoppe et al.; U.S. Pat. No. 2,764,565; issued Sept. 25, 1956, incorporated herein by reference. For purposes of this invention a polyester polyurethane refers to a polyurethane made from a polyester polyol and an organic isocyanate.

The polyester polyurethane foam end wraps used as the starting material for this invention are exemplified in U.S. Pat. No. 3,345,993, Oct. 10, 1967, to Haefele incorporated herein by reference. These end wraps are preferably either square or rectangular in shape and have dimensions within the range from 1⅜ × 1⅜ inches to 4 × 4 inches. An especially preferred size and configuration is a rectangular wafer having the dimensions 3 × 2 inches.

The thickness of the untreated foam end wraps can vary within the range of one sixty-fourth to one-sixteenth inch. As the length and width are increased, a thinner end wrap should be used. Foam end wraps which are thinner than about one sixty-fourth inch are difficult to process and do not have sufficient tear strength for the intended use. End wraps having thicknesses greater than about one-sixteenth inch yield too large a curl. The preferred thickness for the purpose of this invention is one thirty-second inch.

The degree of porosity of the end wrap must be sufficient to permit substantially unimpeded flow of the waving and neutralizing solutions. An average pore incidence from about 30 to about 120 pores per linear inch is necessary for adequate flow. More numerous pores are preferable in the case of thinner end wraps. The preferred end wraps have an average of about 80 pores per linear inch.

Acid Treatment Material

The polyester polyurethane foam end wraps are treated with an acidic material to counteract the effects on hair ends of the keratin-modifying solution. The acid with which the foam end wraps of this invention are treated can be any solid, weak, carboxylic acid having a $pK_1$ varying between about 2.5 and 6 and a water solubility varying between about 0.1 to 10.0 parts acid, preferably 1.0 to 10.0 parts acid, per 100 parts water at 15° C - 20° C. The acid utilized must have $pK_1$ and solubility characteristics within these ranges to insure that the integrity of the polyester polyurethane foam is not impaired. Citric acid, for example, having a high water solubility causes the polyurethane to degrade. The $pK_1$ value should be less than about 6 so excessive amounts of the acid need not be used. As used herein an acid is "solid" if it is in solid form at room temperature, i.e. 20° C.

Examples of suitable carboxylic acids are succinic, itaconic, adipic, azelaic, suberic, pimelic, benzoic, fumaric, mesaconic and o-phthalic acids. Preferred carboxylic acids include succinic, adipic, and itaconic acids. The most preferred acid is adipic acid.

It has been found that the amount of acid present in the foam end wraps of this invention can vary depending on the thickness and outside surface area of the wrap, but a minimum level of 5 milligrams of acid/cubic inch of foam is thought to be required to ensure that protection is obtained. It is preferred, however, that the amount of acid present be from about 9.0 milligrams to about 300 milligrams per cubic inch of foam. This range allows the ends of the hair to be adequately protected while still ensuring that they receive some wave.

End Wrap Preparation

The foam end wrap material may be conveniently treated by use of a water solution of the acid. The material may be passed through the water solution, or the solution may be brushed or sprayed onto the material. The treated material is then dried by means of a drum dryer or oven, air exposure or by other suitable means to remove the moisture present. The concentration of acid in the water solution depends on the acid used, the method of application employed and the acid concentration desired in the treated foam end wraps. The concentration of acid typically would be in the range of about 0.2% to about 60%.

To decrease the likelihood of the end wraps picking up static charge, the foam may be treated with an antistatic material such as a mineral oil mixture.

Hair Waving Method

A preferred embodiment of this invention relates to the process of cold permanent waving. Use of this invention's acid treated foam end wraps in the same manner as conventional end wraps in cold permanent waving reduces the strength of the wave given to the ends of the hair. This is believed to be due to the lowering of the pH of the reducing solution when it comes into contact with the treated foam end wrap which is around the ends of the hair. This results in a softer looking wave, with greater fullness, but with the same strength of curl as current products give except at the hair tips.

More specifically, in regard to the aspect of cold permanent waving processes, this invention comprises the steps of forming the hair into tresses, wrapping around the end of each tress a treated foam end wrap of the type disclosed herein, winding each tress about a cylindrical body, i.e., a curler, saturating each tress with a keratin-reducing composition and thereafter neutralizing the action on the hair of said keratin-reducing composition. Alternatively, the keratin-reducing composition is applied to the hair both before and after the hair is rolled upon curlers.

The keratin-reducing compositions which may be used in the permanent wave processes of this invention contain a water-soluble nonvolatile mercaptan such as mercapto-alkanoic acids, mercapto-acetic acid, mercapto-propionic acid, mercapto-butyric acid and water-soluble salts thereof. Examples of other suitable mercaptans are thioglycolic acid, sodium thioglycolate, potassium thioglycolate, monoethanolamine thioglycolate, β-mercapto isobutyric acid, thiohydracrylic acid, β-mercapto-n-butyric acid, mercapto-caproic acid, thioglycerol and thiolactin acid. These compositions have a pH of 7.0 to 9.5 which can be provided with alkaline agents such as ammonia, monoethanolamine, diisopropylamine, sodium hydroxide, potassium hydroxide and the like.

In addition to the mercaptans, it is often desirable, but not essential, to include in the keratin-reducing composition a water-soluble disulfide of the mercaptan used such as dithiodiglycolic acid, dithiodilactic acid, the disulfides of $\beta$-mercaptobutyric acid, $\beta$-mercaptoisobutyric acid, dithiodihydracrylic acid or a water-soluble salt of these acids to protect against excessive reduction and damage to the hair in accordance with the disclosures in U.S. Pat. No. 2,719,814, Oct. 4, 1955, to Haefele and U.S. Pat. No. 2,719,815, Oct. 4, 1955, to Sanders.

The permanent waving processes of this invention can also be used to advantage in conjunction with pressurized hair waving compositions which are applied to the hair as a fast-breaking foam. Examples of such compositions are disclosed by Banker et al. in U.S. Pat. No. 3,099,603, July 30, 1963, and Sheperd et al. in U.S. Pat. No. 3,103,468, Sept. 10, 1963.

The action on the hair of the keratin-reducing compositions can be neutralized by chemical compounds such as bromates, perborates, hydrogen peroxide or the action of air alone.

End Wrap Exemplification

Certain particular embodiments of the invention are illustrated in the following examples but the invention is not intended to be limited thereto. All percentages used herein previously and subsequently are by weight unless otherwise indicated.

EXAMPLE I

One hundred parts by volume of a polyester of the following composition:

|  | Moles |
|---|---|
| Adipic acid | 16 |
| Diethylene glycol | 16 |
| Trimethylol propane | 1 | are reacted with 47 parts by volume of tolylene diisocyanate in the presence of 10 parts by volume of an activator mixture of the following composition:

|  | Parts by Volume |
|---|---|
| Adipic acid ester of N-diethylaminoethanol | 3 |
| Ammonium oleate | 1 |
| Sulfonated castor oil | 1.5 |
| Water | 1.5 |
| Paraffin oil | 0.5 |

The polyester is mixed with water and the other activator components and then the tolylene diisocyanate is added. The mixture is dried to remove the moisture present. The product is a slab of flexible polyester polyurethane foam of 2.2 pounds per cubic foot density, having an average of 60 cells per linear inch. The slab is then cut into 3 × 2 inch wafers or larger sheets having a thickness of one thirty-second inch.

The reactants and conditions are identified above can be varied in accordance with the teachings of Hoppe et al, U.S. Pat. No. 3,764,565, issued Sept. 25, 1956 to yield foams having an average of 40, 80 and 120 pores per linear inch and thicknesses of one-sixteenth and one sixty-fourth inch.

EXAMPLE II

Foam end wraps measuring 3 × 2 inch × one thirty-second inch made according to Example I were dipped into a 1% aqueous solution of succinic acid ($pK_1 = 4.16$; solubility = 6.8 parts/100 parts $H_2O$ at 20° C.) The amount of solution absorbed by each foam end wrap was 1.0 gram (corresponding to about 53 milligrams of acid/cubic inch of foam). The wraps were then allowed to air dry for a period of about 16 hours at room temperature ($\sim$75° F.).

EXAMPLE III

A sheet of polyurethane foam measuring 15¾ inch × 18¾ inch × 1/32 inch made according to Example I was dipped into a 6.25% aqueous succinic acid solution. The sheet was wrung out until 8.0 grams (corresponding to about 55 milligrams of acid/cubic inch of foam) of the solution were still retained. The sheet was then let air dry for a period of about 4 hours at room temperature ($\sim$75° F). As a final step, individual end wraps measuring 3 × 2 × 1/32 inch were cut from the sheet.

Substantially similar acid treated polyester polyurethane end wraps are realized when in the above Example III preparation, the succinic acid is replaced with an equivalent amount of:

itaconic acid ($pK_1 = 3.85$; solubility = 8.3 parts per 100 parts $H_2O$ at 20° C.)

adipic acid ($pK_1 = 4.43$; solubility = 1.4 parts per 100 parts $H_2O$ at 15° C.)

azelaic acid ($pK_1 = 4.53$; solubility = $\sim$0.24 parts per 100 parts $H_2O$ at 20° C.)

suberic acid ($pK_1 = 4.52$; solubility = 0.14 parts per 100 parts $H_2O$ at 16° C.)

pimelic acid ($pK_1 = 4.71$; solubility = $\sim$5 parts per 100 parts $H_2O$ at 20° C.)

benzoic acid ($pK_1 = 4.19$; solubility = 0.21 parts per 100 parts $H_2O$ at 17.5° C.)

fumaric acid ($pK_1 = 3.03$; solubility = 0.7 parts per 100 parts $H_2O$ at 17° C.)

mesaconic acid ($pH_1 = 3.09$; solubility = $\sim$2.7 parts per 100 parts $H_2O$ at 18° C.); or o-phthalic acid ($pK_1 = 2.89$; solubility = $\sim$0.54 parts per per 100 parts $H_2O$ at 15° C.)

EXAMPLE IV

The acid treated foam end wraps as prepared in accordance with Example II are employed in a permanent waving process using the following keratin-reducing composition

| Component | Weight % |
|---|---|
| Monoethanolamine thioglycolate | 11.41 |
| Hydrogen peroxide | 0.34 |
| Monoethanolamine | 2.30 |
| Mineral oil | 1.555 |
| Oleic acid | 0.337 |
| Potassium hydroxide | 0.088 |
| Ethylene glycol | 0.199 |
| Perfume | 0.50 |
| Polyoxyethylene (23) lauryl ether | 1.043 |
| Color | 0.10 |
| Distilled water | 82.128 |
|  | 100.000 |

The hair is washed and separated into tresses. The acid treated end wrap is folded over the wet hair tress so that it covers all of the free ends. Each wrapped tress is then wound upon a curler and secured. The keratin-reducing composition is applied to the wound tresses and after waiting 15 minutes, rinsed with water and blotted. The head is then covered with a towel and after an additional 30 minutes the hair is neutralized with a 3% hydrogen peroxide solution. The hair is removed from the curlers, again rinsed with water, set in a normal fashion and dried.

The ends of the hair are protected from the total effect of the keratin-reducing composition by the acid treated end wraps.

What is claimed is:

1. An end wrap for use in the permanent waving process which comprises a permeable flexible wafer of open-celled polyester polyurethane foam having a thickness of from about one-sixteenth inch to about one sixty-fourth inch, an average pore incidence within the range of from about 30 to 120 pores per linear inch and, contained in said end wrap, a solid, carboxylic acid having a $pK_1$ of from about 2.5 to about 6.0 and a water-solubility of from about 0.1 to 10.0 parts acid per 100 parts water at 15°–20° C., said acid being present at a level of at least 5 milligrams of acid per cubic inch of foam.

2. An end wrap according to claim 1 wherein the wafer of polyester polyurethane foam has a thickness of 1/32 inch.

3. An end wrap according to claim 1 wherein the wafer of polyester polyurethane foam has an average pore incidence of 80 pores per linear inch.

4. An end wrap according to claim 1 wherein the carboxylic acid is selected from the group of acids consisting of succinic, adipic, itaconic, suberic, azelaic, pimelic, benzoic, fumaric, mesaconic and o-phthalic acids.

5. An end wrap according to claim 4 wherein carboxylic acid is selected from the group consisting of succinic acid, adipic acid and itaconic acid and the amount of acid contained in said end wrap is from about 9 to about 300 milligrams/cubic inch of end wrap.

6. The process of imparting a permanent wave to hair which comprises the steps of forming the hair into tresses, wrapping about the end of each tress a permeable, flexible wafer of polyester polyurethane foam having a thickness of from about one-sixteenth inch to about one sixty-fourth inch, said wafer containing a solid, weak, carboxylic acid having a $pK_1$ of from about 2.5 to about 6.0 and a water solubility of from about 0.1 to 10.0 parts acid per 100 parts water at 15° C. – 20° C., said acid being present at a level of at least 5 milligrams of acid per cubic inch of wafer, winding each tress on a cylindrical body, saturating each wound tress with a keratin-reducing composition and thereafter neutralizing the action on the hair of said keratin-reducing composition.

7. A process according to claim 6 wherein the wafer of polyester polyurethane foam has a thickness of 1/32 inch and an average pore incidence of 80 pores per linear inch.

8. A process according to claim 6 wherein carboxylic acid is selected from the group of acids consisting of succinic, adipic and itaconic acids.

9. A process according to claim 6 wherein the carboxylic acid is adipic acid and the amount of said acid contained in said wafer is from about 9 to about 300 milligrams/cubic inch of wafer.

* * * * *